(12) United States Patent
Kannan et al.

(10) Patent No.: US 9,682,045 B2
(45) Date of Patent: Jun. 20, 2017

(54) STABLE PHARMACEUTICAL COMPOSITIONS OF THYROID HORMONE DRUG

(71) Applicant: CADILA HEALTHCARE LIMITED, Ahmedabad, Gujarat (IN)

(72) Inventors: Muthaiyyan Essakimuthu Kannan, Gujarat (IN); Nitesh Nalinchandra Pandya, Gujarat (IN); Chetan Kacharabhai Patel, Gujarat (IN)

(73) Assignee: CADILA HEALTHCARE LIMITED, Ahmedabad (IN)

( * ) Notice: Subject to any disclaimer, the term of this patent is extended or adjusted under 35 U.S.C. 154(b) by 0 days.

(21) Appl. No.: 14/946,947

(22) Filed: Nov. 20, 2015

(65) Prior Publication Data

US 2016/0143855 A1    May 26, 2016

(30) Foreign Application Priority Data

Nov. 21, 2014  (IN) .......................... 3703/MUM/2014

(51) Int. Cl.
*A61K 31/195* (2006.01)
*A61K 9/20* (2006.01)
*A61K 31/198* (2006.01)
*A61K 31/00* (2006.01)

(52) U.S. Cl.
CPC .......... *A61K 9/2018* (2013.01); *A61K 9/2072* (2013.01); *A61K 9/2077* (2013.01); *A61K 31/00* (2013.01); *A61K 31/198* (2013.01)

(58) Field of Classification Search
USPC ......................................................... 514/567
See application file for complete search history.

(56) References Cited

U.S. PATENT DOCUMENTS

| | | |
|---|---|---|
| 5,225,204 A | 7/1993 | Chen et al. |
| 5,958,979 A | 9/1999 | Lahr et al. |
| 6,555,581 B1 | 4/2003 | Franz et al. |
| 7,067,148 B2 | 6/2006 | Franz et al. |
| 7,195,779 B2 * | 3/2007 | Hanshew, Jr. ........ A61K 9/1623 424/400 |
| 8,008,349 B2 * | 8/2011 | Schreder ............. A61K 9/2063 514/567 |
| 8,293,272 B2 | 10/2012 | Burghart et al. |
| 2013/0053445 A1 * | 2/2013 | Jiang .................... A61K 9/0019 514/567 |

FOREIGN PATENT DOCUMENTS

WO    99/59551 A1    11/1999

OTHER PUBLICATIONS

Patel, H., et al., "The effect of excipients on the stability of levothyroxine sodium pentahydrate tablets", International Journal of Pharmaceutics, 264 (2009), pp. 35-43.

* cited by examiner

*Primary Examiner* — Rei-Tsang Shiao
(74) *Attorney, Agent, or Firm* — Ladas & Parry LP

(57) ABSTRACT

The present invention relates to pharmaceutical compositions comprising a thyroid hormone drug. The invention also relates to processes for the preparation of such compositions.

14 Claims, No Drawings

STABLE PHARMACEUTICAL COMPOSITIONS OF THYROID HORMONE DRUG

FIELD OF THE INVENTION

The invention relates to pharmaceutical compositions comprising a thyroid hormone drug. The invention also relates to processes for the preparation of such compositions.

BACKGROUND OF THE INVENTION

Thyroid hormone drugs are used to treat thyroid hormone deficiency and thyroid hormone replacement therapy in mammals, for example, humans and dogs. In treatment of thyroid hormone deficiency very low daily doses of levothyroxine sodium are used in the range from 25 to 300 mcg. Due to its high potency, it is very important to avoid dosage variations as this may cause serious symptoms of hypothyroidism such as severe depression, fatigue, weight gain, constipation, cold intolerance, swelling, and difficulty concentrating, if levothyroxine sodium is under dosed, or of hyperthyroidism, such as pain, heart palpitations, or cardiac arrhythmias, if levothyroxine sodium dose is too high. Thyroid hormone drugs like levothyroxine or salts thereof are known for its poor stability. Such poorly stable or fast degradation prone drugs may lose its potency over the period of shelf life which may result in under-dosing. Also, there is a common practice to add overages in order to compensate probable potency loss. All such variations of under-dosing or over-dosing of the drug may result in undesirable clinical outcomes. Therefore, storage stability and content uniformity of levothyroxine or salts thereof in the pharmaceutical preparations is a critical issue.

Hypothyroidism is a common condition. It has been reported in the United States Federal Register that hypothyroidism has a prevalence of 0.5 percent to 1.3 percent in adults. In people over 60, the prevalence of primary hypothyroidism increases to 2.7 percent in men and 7.1 percent in women. Because congenital hypothyroidism may result in irreversible mental retardation, which can be avoided with early diagnosis and treatment, newborn screening for this disorder is mandatory in North America, Europe, and Japan.

Thyroid hormone replacement therapy can be a chronic, lifetime endeavor. The dosage is established for each patient individually. The goal of therapy is to achieve and maintain a clinical and biochemical euthyroid state. The goal of suppressive therapy is to inhibit growth and/or function of abnormal thyroid tissue. The dose of levothyroxine sodium tablets, that is adequate to achieve treatment goals depends on a variety of factors including the patient's age, body weight, cardiovascular status, concomitant medical conditions, including pregnancy, concomitant medications, and the specific nature of the condition being treated. Dosing must be individualized and adjustments made based on periodic assessment of the patient's clinical response and laboratory parameters. Generally, the initial dose is small. The amount is increased gradually until clinical evaluation and laboratory tests indicate that an optimal response has been achieved. The dose required to maintain this response is then continued. It has been reported that the dosage increase should be very gradual in patients with myxedema or cardiovascular disease to prevent precipitation of angina, myocardial infarction, or stroke.

Hyperthyroidism is a known risk factor for osteoporosis. Several studies suggest that sub clinical hyperthyroidism in premenopausal women receiving thyroid hormone drugs for replacement or suppressive therapy is associated with bone loss. To minimize the risk of osteoporosis, it is preferable that the dose be kept to the lowest effective dose.

Because of the risks associated with over-treatment or under-treatment with thyroid hormone drug, there is a need for thyroid hormone products that are consistent in potency, bioavailability, and content uniformity. Such consistency is best accomplished by manufacturing techniques that maintain consistent amounts of the active moiety in compositions during its manufacturing process.

Thyroid hormone drugs are natural or synthetic preparations containing tetraiodothyronine ($T_4$, levothyroxine) or triiodothyronine ($T_3$, liothyronine) or both, usually as their pharmaceutically acceptable (e.g., sodium) salts. $T_4$ and $T_3$ are produced in the human thyroid gland by the iodination and coupling of the amino acid tyrosine. $T_4$ contains four iodine atoms and is formed by the coupling of two molecules of diiodotyrosine (DIT). $T_3$ contains three atoms of iodine and is formed by the coupling of one molecule of DIT with one molecule of monoiodotyrosine (MIT). Both hormones are stored in the thyroid colloid as thyroglobulin. Thyroid hormone preparations belong to two categories: (1) natural hormonal preparations derived from animal thyroid, and (2) synthetic preparations. Natural preparations include desiccated thyroid and thyroglobulin.

Desiccated thyroid is derived from domesticated animals that are used for food by man (either beef or hog thyroid), and thyroglobulin is derived from thyroid glands of the hog. The United States Pharmacopoeia (USP) has standardized the total iodine content of natural preparations. Thyroid USP contains not less than (NLT) 0.17 percent and not more than (NMT) 0.23 percent iodine, and thyroglobulin contains not less than (NLT) 0.7 percent of organically bound iodine. Iodine content is only an indirect indicator of true hormonal biologic activity.

Synthetic forms for both $T_4$ and $T_3$ thyroid hormones are available from a number of manufacturers. For example, liothyronine sodium ($T_3$) tablets are available under the trademark Cytomel from King Pharmaceuticals, Inc., St. Louis, Mo. Levothyroxine sodium ($T_4$) is available under the trade name Levoxyl® from King Pharmaceuticals, Inc., under the trade name Synthroid® from Abbvie Inc. Chicago, and under the trade name Unithroid® from Jerome Stevens Pharmaceuticals, Bohemia, N.Y. In addition, a veterinarian preparation of levothyroxine sodium is available under the trade name Soloxine® from King Pharmaceuticals, Inc.

It is well known that the stability of thyroid hormone drugs is quite poor. Also thyroid hormone drugs are hygroscopic and are susceptible to degradation in the presence of moisture, oxygen, and/or light, and under conditions of high temperature. The instability is especially notable in the presence of pharmaceutical excipients, such as carbohydrates, including sucrose, dextrose, and starch, as well as certain dyes. The critical nature of the dosage requirements, and the lack of stability of the active ingredients in the popular pharmaceutical formulations, has led to a crisis which has adversely affected the most prescribed thyroid drug products. See, e.g., 62 Fed. Reg. 43535 (Aug. 14, 1997).

It is desirable, therefore, to prepare stabilized pharmaceutical compositions of thyroid hormone drugs which will have a longer shelf life and reduce the risk associated with degradation products that can be used effectively in the treatment of thyroid hormone deficiency in humans or animals.

U.S. Pat. No. 5,225,204 is directed to improving the stability of levothyroxine sodium. In one embodiment the patent discloses the preparation of stabilized levothyroxine sodium in a dry state by mixing levothyroxine sodium with a cellulose tableting agent using geometric dilution and subsequently combining this mixture with the same or a second cellulose tableting agent, such as microcrystalline cellulose.

U.S. Pat. No. 6,555,581 describes a stabilized immediate release pharmaceutical composition of levothyroxine essentially devoid of carbohydrates. The compositions lose up to 0.3% potency per month during 18 month stability period.

U.S. Pat. No. 7,067,148 describes a stable immediate release pharmaceutical composition of levothyroxine essentially free of carbohydrates wherein the compositions do not lose potency up to about 12.6% w/w during 18 month stability period.

U.S. Pat. No. 5,958,979 describes stabilization of thyroxine preparations by addition of sodium thiosulfate. However, the use of substances like sodium thiosulfate in pharmaceutical preparations is undesirable from the toxicological point of view.

International (PCT) Publication No. WO 99/59551 describes the improvement of storage stability of levothyroxine sodium containing solid pharmaceutical preparations by using gelatin as a binder. As described in the introduction such stabilized formulation has been developed in order to meet the increased requirements on stability as established by the Food and Drug Administration (FDA) in 1996. According to such FDA requirements levothyroxine sodium degradation in tablets throughout their shelf life has been fixed to 10% at the most.

Patel et al. examined the effect of various pH modifying additives on the stability of levothyroxine sodium tablets (Patel H. et al: The effect of excipients on stability of levothyroxine sodium pentahydrate tablets, Int J Pharm 264 (2003) 35-43). It was found that the basic pH modifying additives, sodium carbonate, sodium bicarbonate and magnesium oxide led to improvement of the stability of levothyroxine sodium tablets, whereas acid pH modifying additives, tartaric acid and citric acid led to impairment of stability.

U.S. Pat. No. 8,293,272 discloses stabilized pharmaceutical preparations containing levothyroxine sodium by adjusting the water activity of preparations to values below 0.4. The patent teaches the need to convert levothyroxine pentahydrate form to more stable tetrahydrate form by using specialized drying process. Consequently, the product formulation process becomes lengthy and time consuming. Also, the water activity of the formulation varies with the change of relative humidity during shelf life so that additional measures need to be taken, such as moisture-tight packs, which result in additional costs.

Also, thyroid hormone drugs are hygroscopic and are susceptible to degradation in the presence of moisture, oxygen, and/or light, and under conditions of high temperature. Such degradation of active ingredients results in potency loss which may lead to inadequate dosing. In certain situations, due to poor stability performance, manufacturers released final drug product with a stability "overage" (i.e., more than 100% of the labeled claim) to address the rapid degradation of the product and to allow a practical shelf life meeting desired potency specifications. Such practice also raised concerns of both safety and effectiveness for such products. Thus, there is a need for storage stable pharmaceutical compositions which can maintain the potency of the drug during shelf life thereby avoid the need to add any overages to compensate the potency loss due to such instability problem.

In 2007, the FDA raised the stability requirements on levothyroxine sodium containing products to further diminish the risk associated with degradants generated during shelf life. The limit of levothyroxine sodium degradation in tablets was lowered from 10% to 5% (FDA press release from Oct. 3, 2007).

Thyroid hormone drugs are highly potent drugs. Drugs like levothyroxine are approved at very tow doses of 25 mcg, 50 mcg, 75 mcg, 88 mcg, 112 mcg, 125 mcg, 137 mcg, 150 mcg, 175 mcg, 200 mcg, and 300 mcg for treating thyroid related problems. Also, levothyroxine is needed to be prescribed and administered depending upon the individuals problem need, in order to fulfill an individual's dosing requirements, commercially available tablet dosage forms are provided with a break-line so as to divide the tablet in two or more equal parts. In case of such a potent low dose drug, if the drug is not uniformly distributed throughout the tablet then there will always be a chance that one part may have higher amount of drug than the other part. This may result in either under-dosing or over-dosing of the active ingredients resulting either in sub-therapeutic effects or side and/or toxic effects. Both under-dosing and over-dosing can have deleterious health impacts. In the case of under-dosing, a sub-optimal response and hypothyroidism could result. Under-dosing has also been reported to be a potential factor in decreased cardiac contractility and increased risk of coronary artery disease. Conversely, the over-dosing may result in toxic manifestations of hyperthyroidism such as cardiac pain, palpitations, or cardiac arrhythmia's. In patients with coronary heart disease, even a small increase in the dose of levothyroxine sodium may be hazardous in a particular patient. Thus, content uniformity and uniform distribution of the drug throughout the dosage form is of paramount importance.

There is an ongoing demand for thyroid hormone drug pharmaceutical compositions having an improved stability and content uniformity. The pharmaceutical compositions should ensure uniform drug distribution throughout the formulation, should not comprise any toxicologically unacceptable adjuvants, and should be capable of storage in a stable manner over an extended period of time.

SUMMARY OF THE INVENTION

In one general aspect, there is provided a stable pharmaceutical composition comprising a thyroid hormone drug or pharmaceutically acceptable salts thereof, at least one carbohydrate, wherein the carbohydrate is a saccharide, and one or more pharmaceutically acceptable excipients.

Embodiments of the pharmaceutical composition may include one or more of the following features. For example, the pharmaceutically acceptable excipient may include a diluent, a binder, a lubricant, a surfactant, a disintegrant, a glidant, an antioxidant, a sweetener, a flavoring agent, a solvent, and the like.

In another general aspect, there is provided a stable pharmaceutical composition comprising a thyroid hormone drug or pharmaceutically acceptable salts thereof, at least one carbohydrate, at least one diluent and one or more pharmaceutically acceptable excipients.

Embodiments of the pharmaceutical composition may include one or more of the following features. For example, the pharmaceutically acceptable excipient may include a binder, a lubricant, a surfactant, a disintegrant, a glidant, an antioxidant, a sweetener, a flavoring agent, a solvent, and the like.

In another general aspect, there is provided a stable pharmaceutical composition comprising a thyroid hormone drug or pharmaceutically acceptable salts thereof, at least one carbohydrate, at least one diluent, at least one antioxidant, and one or more pharmaceutically acceptable excipients.

Embodiments of the pharmaceutical composition may include one or more of the following features. For example, the pharmaceutically acceptable excipient may include a binder, a lubricant, a surfactant, a disintegrant, a glidant, a sweetener, a flavoring agent, a solvent, and the like.

In another general aspect, there is provided a stable pharmaceutical composition comprising a thyroid hormone drug or pharmaceutically acceptable salts thereof, at least one carbohydrate, and one or more pharmaceutically acceptable excipients, wherein the composition retains at least 95% of the potency of thyroid hormone drug in the composition after storage for 24 months at 25° C. and 60% relative humidity.

In another general aspect, there is provided a stable pharmaceutical composition comprising thyroid hormone drug or pharmaceutically acceptable salts thereof, at least one carbohydrate, and one or more pharmaceutically acceptable excipients, wherein the composition retains at least 95% of the potency of thyroid hormone drug in the composition after storage for about 3 months at 40° C. and 75% relative humidity.

In still another general aspect, there is provided a stable tablet composition comprising a thyroid hormone drug or pharmaceutically acceptable salts thereof having at least one break-line wherein the break-line divides the tablet in equal parts having substantially equal levothyroxine dosage.

In another general aspect, there is provided a process for preparing a pharmaceutical composition of a thyroid hormone drug or pharmaceutically acceptable salts thereof. The process includes:
  a) blending one or more carbohydrates, diluents and binders together;
  b) dissolving or dispersing the thyroid hormone drug and an antioxidant in a granulating fluid, optionally including a surfactant;
  c) granulating the blend of step (a) with a solution/dispersion of step (b);
  d) drying and sizing the granules;
  e) mixing the sized granules with a carbohydrate, a disintegrant, a lubricant and optionally a diluent; and
  f) filling either into capsules or compressing into tablets dosage form, optionally coating the tablets with a functional or a non-functional coating.

In another aspect, there is provided a process for preparing a pharmaceutical composition of a thyroid hormone drug or pharmaceutically acceptable salts thereof. The process includes preparing base granules comprising (a) blending one or more carbohydrates, diluents and binders together, (b) dissolving or dispersing a thyroid hormone drug and an antioxidant in a granulating fluid, optionally including a surfactant, (c) granulating the blend of step (a) with a solution/dispersion of step (b), and (d) drying and sizing the granules; preparing placebo granules comprising (a) blending carbohydrates, diluents, antioxidant, and binder together and granulating with a granulating fluid, and (b) drying and sizing the granules; and mixing both the granules together and further blending with a carbohydrate, a disintegrant, a lubricant, and a diluent, and compressing into a tablet dosage form, optionally coating the tablets with a functional or a non-functional coating.

In a further general aspect, there is provided a pharmaceutical packaging means comprising plurality of unit dosage of a thyroid hormone drug or pharmaceutically acceptable salts thereof and a moisture absorber and/or oxygen scavenger.

In another general aspect, there is provided a kit comprising a blister type pharmaceutical package comprising unit dose pharmaceutical composition and a moisture absorber and/or oxygen scavenger, wherein the moisture absorber and/or oxygen scavenger is placed along with the material comprising the pharmaceutical package.

In another general aspect, there is provided a blister type pharmaceutical package comprising unit dose pharmaceutical composition and a moisture absorber and/or oxygen scavenger wherein the pharmaceutical package is labeled with a numerical value or specific mark that conveys the patient and/or care taker regarding chronological removal of the dosage from the package.

The details of one or more embodiments of the present invention are set forth in the description below. Other features, objects, and advantages of the invention will be apparent from the description.

DETAILED DESCRIPTION OF THE INVENTION

The present invention relates to storage stable oral pharmaceutical compositions of a thyroid hormone drug or pharmaceutically acceptable salts thereof and methods by which they are produced. The methods involve a granulation step comprising a thyroid hormone drug and one or more saccharides to provide a formulation having better stability of both the granulation intermediates and the final oral dosage forms prepared from these granulation intermediates. Thus, the present inventors have developed a stable dosage formulation in which the dosage of a thyroid hormone drug is maintained at a predictable level for a longer period of time without a need of adding drug overages.

The methods and formulations of this invention take advantage of the finding that including a saccharide in the formulation results in a surprisingly stable thyroid hormone drug composition. This invention can be used to produce stable formulations of any natural or synthetic thyroid hormone replacement drug. Therefore, although the following description and example refer to compositions and methods using levothyroxine or salts thereof, the invention is understood to encompass other thyroid hormone medications of the general formula

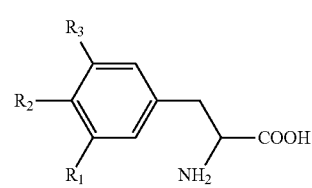

wherein $R_1$ and $R_3$ may be the same or different and are selected from hydrogen; halogen; alkyl; aryl; cycloalkyl; heterocycloalkyl; amide; alcohol; acid; ester; ether; acyl; alkenyl; and alkynyl; wherein $R_2$ is

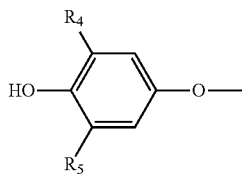

wherein $R_4$ and $R_5$ may be the same or different and are selected from hydrogen; halogen; alkyl; aryl; cycloalkyl; heterocycloalkyl; amide; alcohol; acid; ester; ether; acyl; alkenyl; and alkynyl. The medication can be in the form of a free acid, a free base, an organic salt, an inorganic salt, or a hydrate. Liothyronine is an example of a drug encompassed by the above-mentioned general formula.

According to this invention, stabilized pharmaceutical compositions are produced by contacting the active ingredient with a saccharide such as a monosaccharide or a disaccharide to form granules. Further, additional excipients may be added for preparing desired granules. Generally, further pharmaceutical excipients are added to produce final oral dosage forms such as tablets or capsules.

The term "levothyroxine" includes not only the levothyroxine per se but also its pharmaceutically acceptable salts, pharmaceutically acceptable solvates, pharmaceutically acceptable hydrates, pharmaceutically acceptable enantiomers, pharmaceutically acceptable derivatives, pharmaceutically acceptable polymorphs and pharmaceutically acceptable prodrugs thereof, and their crystalline and amorphous forms.

Formulations of levothyroxine with greatly increased resistance to degradation can be produced by providing excipients which reduce or eliminate degradation of the active substance. Although the prior art indicates that reaction between levothyroxine sodium and certain carbohydrate, monosaccharide or disaccharide excipients is responsible for the poor stability of the drug, the present inventive formulation achieves surprisingly stable levothyroxine dosage forms using these previously disfavored excipients.

The inventors of the present invention surprisingly found that it is possible to develop a stable pharmaceutical composition of levothyroxine or salts thereof and a saccharide. The composition prevents potency loss of said levothyroxine not more than about 5% w/w for a period of at least about 24 months after storage at 25° C. and 60% RH.

The pharmaceutical composition according to the present invention comprises levothyroxine and a saccharide, isomalt, wherein the levothyroxine is uniformly mixed along with isomalt. Both of the ingredients can be mixed uniformly using any process known in the art, such as simple mixing, blending, sieving, co-milling, and the like. The composition shows stability for a period of at least about 24 months after storage at 25° C. and 60% RH. Such a stable composition will maintain potency of the levothyroxine or salts thereof from the dosage form which will provide sufficient dose to the patient and thus reduces the chances of under-dosing and better clinical outcome as compared to prior art formulations.

The pharmaceutical compositions of this invention may be prepared for administration orally, rectally, vaginally, transmucosally, transdermally, parenterally, subcutaneously, and intramuscularly. The pharmaceutically acceptable excipients which are suitable for use in formulations for these methods of administration are known to those of skill in the art and may be included in the formulations according to this invention. Generally, excipients contemplated for use in the inventive formulations may include, but are not limited to adjuvants; preservatives; buffers; fillers, extenders, carriers, binders, disintegrants, carbohydrates, and diluents; glidants and lubricants; surfactants, wetting agents and surface active agents; suspending agents and solvents. Compounds such as dyes and colorants, sweeteners, flavorings, perfuming agents and taste-masking ingredients also may be included in the formulations according to this invention. Any pharmaceutically acceptable excipient, such as ingredients to aid in processing or to improve taste or appearance is contemplated for use with these formulations. Further excipients may be included according to the judgment of the pharmaceutical scientist formulating the medicament. In addition, other active ingredients may be included to produce a dual or multiple ingredient medication.

Solid dosage forms which may be prepared according to this invention can include tablets, capsules, rectal or vaginal suppositories, pills, dragees, lozenges, granules, beads, microspheres, pellets and powders, or any combination thereof. Formulations also may be prepared in the form of solutions, suspensions, emulsions, syrups and elixirs. These liquid dosage forms may include liquid diluents in addition to the solid ingredients discussed above. Such diluents may include, but are not limited to, solvents, solubilizing agents, suspending agents and emulsifiers such as water or saline solutions, ethanol and other pharmaceutically acceptable alcohols, ethyl carbonate, ethyl acetate, propylene glycol, dimethyl formamide, pharmaceutically acceptable oils such as cottonseed, corn, olive, castor and sesame, fatty acid esters of sorbitan, polyoxyethylene sorbitol, and agar-agar. Formulations can be either of immediate or modified release in nature.

In one of the general embodiments, the tablet compositions is provided with a break-line in order to divide the tablet in two or more equal parts for fulfilling an individual's dosing requirements. Since drug is uniformly distributed throughout the dosage form, the patient will always receive the correct required dose. This will result in optimal dosing of the drug and better treatment outcome.

Suitable carbohydrates may include saccharides, i.e., monosaccharides, disaccharides, polysaccharides, are selected from one or more of isomalt, arabinose, dextrose, sucrose, fructose, maltose, trehalose, and the like. The amount of the carbohydrate is preferably from about 0.05% to about 99.95%, preferably from about 1% to about 90%, more preferably from about 10% to about 75% by weight of the composition. According to one of the variation, the composition of the invention may devoid of lactose.

In one of the preferred embodiment, the pharmaceutical composition of the invention comprises about 75% of carbohydrate by total weight of the composition.

Suitable diluents are selected from, but are not limited to, cellulose derivatives such as microcrystalline cellulose, croscarmellose sodium, carbohydrates such as isomalt, arabinose, dextrose, sucrose, fructose, maltose, trehalose, and sugar alcohols such as mannitol, erythritol, sorbitol, xylitol lactitol, and derivatives thereof. The amount of the diluents is preferably from about 0.05% to about 99.95%, preferably from about 5% to about 50%, more preferably from about 10% to about 20% by total weight of the composition.

Suitable surfactants which may be used in the pharmaceutical composition of the invention include, for example, both non-ionic and ionic (cationic, anionic and zwitterionic) surfactants such as sodium lauryl sulfate, poloxarners (copolymers of polyoxyethylene and polyoxypropylene), natural or synthetic lecitins, sorbitan esters, polyoxyethylene sorbitan fatty acid esters, polyoxyethylene castor oil derivatives, polyoxyethylene stearates, ethoxylated cholesterins, commercially available as Solulan™ vitamin derivatives, e.g. vitamin E derivatives such as tocopherol polyethylene glycol succinate (TPGS), sodium dodecyl sulfate or sodium laurylsulfate; a bile acid or salt thereof, for example cholic acid, glycolic acid, or mixtures thereof. The amount of the surfactant is preferably from about 0.01% to about 5% by total weight of the composition.

Suitable disintegrants may include one or more of, but are not limited to starches such as maize starch and rice starch, cross-linked N-vinyl-2-pyrrolidone (CLPVP), sodium starch glycolate, croscarmellose sodium, low-substituted hydroxypropyl cellulose, cross-linked sodium carboxymethyl cellulose, swellable ion exchange resins, alginates and combinations thereof. A preferred disintegrant is CLPVP for example as marketed under the trade names POLYPLASDONE XL and POLYPLASDONE XL-10. A preferred croscarmellose sodium is marketed under the trade name Ac-Di-Sol. A preferred sodium starch glycolate is marketed under the trade names EXPLOTAB and EXPLOTAB CLV. The amount of the disintegrant is preferably from about 0.1% to about 10%, preferably from about 0.5% to about 5%, more preferably from about 1% to about 3% by weight of the composition.

In one of the preferred embodiment, the preferred disintegrant used in the pharmaceutical composition is crospovidone. The amount of crospovidone is about 2% based on the total weight of the composition.

Suitable glidants may include one or more of, but are not limited to silicon dioxide, colloidal silicon dioxide, stearic acid, magnesium stearate, calcium stearate, talc, hydrogenated castor oil, sucrose esters of fatty acids, microcrystalline wax, yellow beeswax, white beeswax and the like, or mixtures thereof.

Suitable hydrophilic lubricants may include one or more of sodium stearyl fumarate, polyethylene glycols, sodium stearyl sulfate, cocoa butter, sodium benzoate, and the like.

Suitable hydrophobic lubricants may include, but are not limited to, stearic acid and its derivatives or esters like sodium stearate, magnesium stearate and calcium stearate; talc and colloidal silicon dioxide.

Suitable antioxidant may include, but are not limited to ascorbic acid, citric acid, ascorbyl palmitate, butylated hydroxyanisole, a mixture of 2 and 3 tertiary-butyl-4-hydroxyanisole, butylated hydroxytoluene, butylated hydroxy anisole, sodium isoascorbate, dihydroguaretic acid, potassium sorbate, sodium bisulfate, sodium metabisulfate, sorbic acid, potassium ascorbate, vitamin E, 4-chloro-2,6-ditertiarybutylphenol, alphatocopherol, and propylgallate.

Suitable binders may include one or more of methyl cellulose, hydroxypropyl cellulose (HPC), hydroxypropyl methyl cellulose (HPMC), starch, polyvinylpyrrolidone (PVP), gelatin, alginate, gum arabic, ethyl cellulose, polyvinyl alcohol, tragacanth, sodium alginate, microcrystalline cellulose, sorbitol, sodium chloride, chitosan, hydrogenated vegetable oil, kaolin, glycerol palmitostearate, magnesium carbonate, sodium citrate, dicalcium phosphate and other alkaline inorganic salts, carboxylmethylcellulose and other cellulose polymers, and calcium carbonate, and equivalents thereof.

Preferably, the binder used in the formulation is polyvinylpyrrolidone. The binder is preferably added in a quantity ranging from about 0.1% to 15% by weight of composition.

Suitable granulating solvents may include purified water, methanol, ethanol, Isopropyl alcohol, dichloro methane, acetone, and combinations thereof.

In one of the general embodiments, the compositions of the invention can be packed into a unit pharmaceutical package such as a strip pack or blister pack and bulk pharmaceutical pack such as High-density polyethylene (HDPE) and polyethylene teraphthalate (PET) bottle having thickness ranging from 0.6 mm to 2.5 mm. The package may further comprise one or more moisture absorber and/or oxygen scavenger.

In another embodiment, a pharmaceutical package may comprise a pharmaceutical composition and a moisture absorber and/or oxygen scavenger.

In case where the unit pharmaceutical pack is a strip pack or a blister pack, it is desirable that the moisture absorber and/or oxygen scavenger is contained in the material composing the packaging component by inserting a resin integrated with the moisture absorber and/or oxygen scavenger in the blister material resin. It is also desirable that outer layer is one having a high barrier property, and that a moisture absorber and/or oxygen scavenger is contained in materials for the packaging component by being coated or laminated at the inside of the blister material resin, or by directly being integrated (e.g., mixed) with the blister material.

The blister pack may be in the form of a fish bone pack wherein a disc, containing moisture absorber or oxygen scavenger may be placed in a blister connected to other blister containing thyroid hormone pharmaceutical compositions.

According to one of the embodiments, the fish bone package is labeled with dosing administration direction which suggest the patient and/or care taker to remove pharmaceutical composition first which is more distant from the disc. Alternatively, these individual units of the blister package may be labeled with a numerical value or specific mark that conveys the patient and/or care taker regarding chronological removal of dosage from the package.

In further embodiments, examples of the moisture absorber to be used in the present invention include activated carbon, calcium chloride, metallic oxide, such as an alkaline earth metallic oxide (e.g. calcium oxide (CaO) etc.), an alkaline earth metallic hydroxide (e.g. calcium hydroxide etc.), sulfate of an alkaline earth metal (e.g. magnesium sulfate, calcium sulfate, etc.), silicon dioxide (silica gel), a bonded product of alumina oxide and silicon dioxide (silica alumina), alumina oxide (active alumina), natural or synthetic zeolite (molecular sieves 3A, 4A, SA, 13X), allophane, clay, a mixture of clay and activated carbon, a mixture of silica gel and activated carbon, a mixture of silica gel and clay, a mixture of silica alumina and activated carbon, a mixture of synthetic zeolite and activated carbon, a mixture of allophane and activated carbon (e.g., allophane added with activated carbon, or allophane kneaded with activated carbon etc.), pulp containing silica gel (e.g., ultrafine silica gel mixed between paper fibers, silica gel packaged in paper tube etc.), pulp containing calcium chloride (e.g., paper material impregnated with liquid calcium chloride, dried and coated with film etc.), pulp containing allophane (e.g., pulp impregnated with allophane liquid, dried and film coated, allophane packaged in paper tube etc.), and the like.

In further embodiments, examples of the oxygen scavengers to be used in the present invention include metal-based absorbers such as particulate-type iron (e.g., hydrogen reduced iron, electrolytically reduced iron, atomized iron, and milled pulverized iron powders), copper powder, zinc powder, ferrous carbonate and a metal halide catalyst, ascorbic acid, butylated hydroxylanisole, butylated hydroxyltoluene, activated carbon, vitamin E, propyl gallate, β-carotene, and the like.

In one embodiment, a formulation can be prepared using the following general steps:
a) blending one or more carbohydrates, diluents and binders together;
b) dissolving or dispersing levothyroxine and an antioxidant in a granulating fluid, optionally comprising a surfactant;
c) granulating the blend of step (a) with a solution/dispersion of step (b);
d) drying and sizing the granules;
e) mixing the sized granules with a carbohydrate, a diluent, a disintegrant, a lubricant, and optionally diluent; and
f) filling the lubricated granules into capsules or compressing into a tablet dosage form, optionally coating the tablets with a functional or a non-functional coating.

In another preferred embodiment, a formulation can be prepared using the following general steps:

Step (1) Preparation of base granules:
a) blending one or more carbohydrates, diluents and binders together;
b) dissolving or dispersing levothyroxine and an antioxidant in a granulating fluid, optionally comprising a surfactant;
c) granulating the blend of step (a) with a solution/dispersion of step (b); and
d) drying and sizing the granules Step (2) Preparation of placebo granules:
a) blending carbohydrates, diluents, antioxidants, and binders together and granulated with a granulating fluid;
b) drying and sizing the granules; and Step (3) mixing both the granules together and further blending with a carbohydrate, a disintegrant, a lubricant and optionally a diluent; and
filling the lubricated granules into capsules or compressing into a tablet dosage form, optionally coating the tablets with a functional or a non-functional coating.

Example 1

Levothyroxine sodium tablets were manufactured by separately preparing base granules comprising levothyroxine sodium and placebo granules and mixing them in appropriate proportion and compressing them into a tablet dosage form.

TABLE 1

Composition of base granules

| Ingredients | Formulation 1 (mg) | Formulation 2 (mg) | Formulation 3 (mg) |
|---|---|---|---|
| Levothyroxine sodium | 0.088 | 0.137 | 0.300 |
| Isomalt | 65.750 | 65.700 | 65.540 |
| Microcrystalline cellulose | 22.442 | 22.442 | 22.442 |
| Butylated hydroxyanisote | 0.020 | 0.020 | 0.020 |
| Povidone K 30 | 0.750 | 0.750 | 0.750 |
| Granulating solvent | q.s. | q.s. | q.s. |

Process for preparing base granules: Levothyroxine sodium, isomalt, microcrystalline cellulose, butylated hydroxy anisole were mixed together uniformly and granulated with a granulating solvent.

TABLE 2

Composition of placebo granules

| Ingredients | Theoretical Qty/Tablet (mg) |
|---|---|
| Isomalt | 65.838 |
| Microcrystalline cellulose | 22.442 |
| Butylated hydroxyanisole | 0.020 |
| Povidone K 30 | 0.750 |
| Granulating solvent | q.s. |

Process for preparing placebo granules: Isomalt, microcrystalline cellulose, butylated hydroxyanisole were mixed together and granulated with a granulating solvent.

TABLE 3

Formulation of levothyroxine sodium Tablets (25 mcg)

| Ingredients | Theoretical Qty/Tablet (mg) |
|---|---|
| Base granules (equivalent quantity of granules from Formulation 1) | 25.298 |
| Placebo granules | 63.752 |
| Colloidal silicon dioxide | 0.650 |
| Silicon dioxide | 0.650 |
| Crospovidone | 1.950 |
| Sodium lauryl sulfate | 0.130 |
| Isomalt | 33.945 |
| Magnesium stearate | 3.250 |
| FD&C yellow No 6 AL Lake | 0.375 |

Preparation of levothyroxine sodium tablets: 25 mcg: Equivalent quantity of base granules prepared according to Example 1 and placebo granules were mixed uniformly and further blended with colloidal silicon dioxide, silicon dioxide, crospovidone, sodium lauryl sulfate, isomalt, magnesium stearate, lake dye and compressed into tablets.

Further, this is within the purview of a skilled artisan to prepare tablets of different strengths using base granules either of formulation 1, 2, and 3 and mixing with required amount of placebo granules, further blending with additional excipients and compressing into a tablet dosage form.

Stability Study:

Table 4 represents the stability data of levothyroxine sodium tablets stored at 25° C./60% relative humidity (RH) for up to 24 months in 40 cc HDPE bottle. Stability evaluation was done using assay method on the stored tablet at regular interval. Assay results demonstrate that the tablet composition prepared according to Example 1 were stable for 24 months at 25° C./60% relative humidity.

TABLE 4

Stability study data of levothyroxine sodium Tablets 25/300 mcg at 25° C./60% relative humidity

| Period in Months | Assay Levothyroxine Sodium Tablets | |
|---|---|---|
| | 25 mcg | 300 mcg |
| Initial | 101.0 | 100.2 |
| 3 | 102.0 | 99.4 |
| 6 | 100.1 | 96.8 |
| 9 | 100.8 | 97.3 |
| 12 | 101.8 | 96.3 |

TABLE 4-continued

Stability study data of levothyroxine sodium Tablets
25/300 mcg at 25° C./60% relative humidity

| Period in Months | Assay Levothyroxine Sodium Tablets | |
|---|---|---|
| | 25 mcg | 300 mcg |
| 18 | 98.0 | 95.8 |
| 24 | 98.3 | 96.4 |

Table 5 represents the stability data of levothyroxine tablets stored at 40° C./75% RH for up to 3 months in 40 cc HDPE bottle. Assay results demonstrate that the tablet composition prepared according to Example 1 were stable for 3 months at 40° C./75% relative humidity.

TABLE 5

Stability study data of levothyroxine sodium Tablets
25/300 mcg at 40° C./75% relative humidity

| Period in Months | Assay of Levothyroxine Sodium Tablets | |
|---|---|---|
| | 25 mcg | 300 mcg |
| Initial | 101.0 | 100.2 |
| 1 | 101.5 | 97.5 |
| 2 | 100.7 | 97.2 |
| 3 | 98.0 | 98.4 |

Content Uniformity Study:

Content Uniformity was determined by assay method of levothyroxine sodium from its tablets compositions. Content uniformity study was performed on levothyroxine sodium tablets 25 mcg, 50 mcg, 75 mcg, 88 mcg, 100 mcg, 112 mcg, 125 mcg, 137 mcg, 150 mcg, 175 mcg, 200 mcg, and 300 mcg and also on equivalent commercially available levothyroxine tablets compositions; Synthroid®, Levoxyl®, and Unithroid®.

Content uniformity study was carried out by assay method on 10 tablets from each composition. The content uniformity is acceptable if acceptance value is equal to 15 for L1 & 25 for L2, calculated according to following formula $$|M-\overline{X}|+ks$$

Where,

M is reference value $\overline{X}$ is mean of individual content expressed as a percentage of the label claim k is acceptability constant, and s is sample standard deviation

TABLE 6

Comparative content uniformity data for compositions prepared according to invention and commercially available products.

| Strength | Formulations according to invention (AV) | Synthroid ® (AV) | Levoxyl ® (AV) | Unithroid ® (AV) |
|---|---|---|---|---|
| 25 mcg | 1.8 | 2.9 | 3.5 | 16.4 |
| 50 mcg | 2.6 | 3.4 | 1.8 | 13.0 |
| 75 mcg | 2.1 | 2.9 | 5.9 | 6.7 |
| 88 mcg | 1.5 | 1.0 | 3.5 | 11.3 |
| 100 mcg | 2.4 | 7.4 | 7.5 | 9.1 |
| 112 mcg | 2.9 | 3.9 | 10.5 | 14.3 |
| 125 mcg | 1.2 | 3.8 | 3.3 | 8.9 |
| 137 mcg | 1.4 | 8.1 | 9.5 | — |
| 150 mcg | 4.8 | 4.3 | 10.0 | 8.2 |
| 175 mcg | 2.9 | 6.5 | 3.4 | 12.7 |
| 200 mcg | 2.2 | 8.3 | 4.3 | 4.0 |
| 300 mcg | 2.9 | 2.4 | — | 6.5 |

Breakability Study:

Breakability study was performed on levothyroxine sodium tablets 25 mcg and 300 mcg. For performing the study, tablets were broken into two parts along the break-line presented on the tablets. The tablets were split into two equal parts using manual process, i.e., manually by applying pressure along the break-line and with the help of a tablet splitter. The split tablets were assayed for determining the amount of levothyroxine in each of the parts of the tablets.

TABLE 7

Assay results of levothyroxine sodium split tablet in two equal parts

| Formulation | Assay (tablet splitted manually) | Assay (tablet splitted with splitter) |
|---|---|---|
| 25 mcg | 102.2 | 100.9 |
| 300 mcg | 100.6 | 100.31 |

EXAMPLE 2

Formulation according to Example 2 was prepared using the process according to Example 1.

TABLE 8

Composition of Example 2

| Ingredients | Formulation I (mg) |
|---|---|
| Levothyroxine sodium | 0.025 |
| Isomalt | 65.000 |
| Lactose monohydrate | 6.500 |
| Croscarmellose sodium | 3.900 |
| Microcrystalline cellulose | 16.005 |
| Butylated hydroxyanisote | 0.020 |
| Povidone K 30 | 1.500 |
| Granulating solvent | q.s. |
| Colloidal silicon dioxide | 0.350 |
| Sodium lauryl sulfate | 0.650 |
| Isomalt | 32.500 |
| Magnesium stearate | 3.250 |
| FD&C yellow No 6 AL Lake | 0.300 |

Formulations prepared according to Example 2 and Example 1 (table 3) was compared for studying impact of isomalt on the stability of levothyroxine in its tablet compositions. Table 9 compares impurity profile of formulations according to Example 2 and Example 1 (table 3). Study results shows that formulation of Example 1 comprising isomalt is more stable as compared to formulation of Example 2.

TABLE 9

Impurity Profile
Levothyroxine Tablets - Impurity Profile

| Related Compounds | Example 2 | Example 1 |
|---|---|---|
| Liothyronine sodium | 0.141 | 0.114 |
| Tetraiodothyroacetic acid | 0.386 | 0.185 |
| Triiodothyroacetic acid or T3 - acetic acid | ND | ND |
| Maximum unknown individual impurity | 0.544 | 0.058 |
| Total impurities | 1.796 | 0.719 |

Table 9 represents the impurity profile of levothyroxine tablets after stored at 40° C./75% RH for 3 months.

While the invention has been described in terms of its specific embodiments, certain modifications and equivalents will be apparent to those skilled in the art and are intended to be included within the scope of the invention.

We claim:

1. A stable oral pharmaceutical composition comprising levothyroxine sodium, one or more carbohydrates selected from the group consisting of isomalt, arabinose, dextrose, sucrose, fructose, maltose and trehalose, and one or more pharmaceutically acceptable excipients, wherein the composition retains at least 95% of the potency of levothyroxine sodium after storage for 24 months at 25° C. and 75% relative humidity.

2. The stable oral pharmaceutical composition according to claim 1, wherein the composition comprises from about 1 to about 95% by weight of the carbohydrates based on the total weight of the composition.

3. The stable oral pharmaceutical composition according to claim 1, wherein the carbohydrate is isomalt.

4. The stable oral pharmaceutical composition according to claim 3, wherein the stable composition comprises about 75% by weight of isomalt based on the total weight of the composition.

5. The stable oral pharmaceutical composition according to claim 1, wherein the composition is a tablet.

6. The stable oral pharmaceutical composition according to claim 1, wherein the pharmaceutically acceptable excipients comprise one or more of diluents, binders, lubricants, surfactants, disintegrants, and antioxidants.

7. The stable oral pharmaceutical composition according to claim 1, wherein the composition is prepared by a wet granulation process.

8. The stable oral pharmaceutical composition according to claim 7, wherein the wet granulation process comprises the following steps:
   a) blending one or more carbohydrates, diluents and binders together;
   b) dissolving or dispersing a levothyroxine sodium and an antioxidant in a granulating fluid, optionally including a surfactant;
   c) granulating the blend of step (a) with the solution/dispersion of step (b);
   d) drying and sizing the granules;
   e) mixing the sized granules with one or more carbohydrates, disintegrants, lubricants and optionally diluents; and
   f) preparing the pharmaceutical composition comprising the granule blend of step (e).

9. The stable oral pharmaceutical tablet composition according to claim 5 having a break-line, wherein the break-line allows the tablet to be divided in two equal parts having substantially equal amounts of the levothyroxine sodium.

10. The stable oral pharmaceutical composition according to claim 9, wherein the tablet composition comprises one or more carbohydrates and one or more pharmaceutically acceptable excipients.

11. The stable oral pharmaceutical composition according to claim 10, wherein the tablet composition comprises from about 1 to about 95% by weight of the carbohydrates based on the total weight of the composition.

12. The stable oral pharmaceutical composition according to claim 10, wherein the pharmaceutically acceptable excipients comprise one or more diluents, binders, lubricants, surfactants, disintegrants, and antioxidants.

13. The stable oral pharmaceutical composition comprising according to claim 1, wherein the composition does not contain more than 1% w/w of total impurities after storage for 3 months at 40° C./75% relative humidity.

14. The stable oral pharmaceutical composition according to claim 1, wherein the composition does not contain more than 0.3% w/w of related impurity tetraiodothyroacetic acid after storage for 3 months at 40° C./75% relative humidity.

* * * * *